United States Patent [19]

Masuho et al.

[11] 4,450,154
[45] May 22, 1984

[54] ANTITUMOR HYBRID AND PROCESS FOR THE PREPARATION THEREOF

[75] Inventors: Yasuhiko Masuho, Hino; Takeshi Hara, Hachioji, both of Tokyo, Japan

[73] Assignee: Teijin Limited, Tokyo, Japan

[21] Appl. No.: 333,214

[22] Filed: Dec. 21, 1981

Related U.S. Application Data

[62] Division of Ser. No. 170,332, Jul. 21, 1980, Pat. No. 4,350,626.

[30] Foreign Application Priority Data

Jul. 20, 1979 [JP] Japan .................................. 54-91634

[51] Int. Cl.³ ..................... C07G 7/00; A61K 37/00; C07C 103/52
[52] U.S. Cl. ................................ 260/112 R; 424/177; 260/112.5 R
[58] Field of Search .................... 260/112.5 R, 112 R; 424/177

[56] References Cited

U.S. PATENT DOCUMENTS 4,296,090 10/1981 Graham, Jr. et al. ........ 260/112.5 R
4,302,386 11/1981 Stevens ......................... 260/112.5 R
4,350,626 9/1982 Masuho et al. ............... 260/112.5 R
4,351,764 9/1982 Birr .............................. 260/112.5 R Primary Examiner—Delbert R. Phillips
Attorney, Agent, or Firm—Sughrue, Mion, Zinn, Macpeak and Seas

[57] ABSTRACT

Antitumor protein hybrid, composed of a moiety which is substantially the fragment Fab of an antitumor immunogloblin and a moiety which is the subunit A of ricin, which is expressed by the following formula (I):

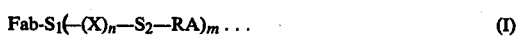

$$\text{Fab-S}_1(-(X)_n-S_2-RA)_m \ldots \tag{I}$$

(where Fab indicates a moiety which is substantially the fragment Fab of an antitumor immunogloblin; RA indicates a moiety which is the subunit A of ricin; X indicates a divalent organic radical; $S_1$ and $S_2$ are both sulfur atoms, $S_1$ indicating a sulfur atom arising from the disulfide bond (—S—S— bond) in an immunoglobulin and $S_2$ a sulfur atom arising from the disulfide bond in ricin; n stands for 0 or 1 and m stands for an integer of 1 to 5). This antitumor protein hybrid has remarkable and specific cytotoxicity against tumor cells.

3 Claims, 4 Drawing Figures

ANTITUMOR HYBRID AND PROCESS FOR THE PREPARATION THEREOF

CROSS REFERENCE TO RELATED APPLICATIONS

This application is a divisional application of Ser. No. 170,332, filed July 21, 1980, now U.S. Pat. No. 4,350,626.

BACKGROUND OF THE INVENTION

1. Field of the Invention

The present invention relates to a novel antitumor protein hybrid, for example, cytotoxic against mouse tumors, and a process for the preparation thereof. More particularly, the present invention relates to a novel protein hybrid, which, having a moeity which is substantially the fragment Fab of an antitumor immunoglobulin and a moiety which is the subunit A of plant toxin ricin, is specifically useful as a remedy for malignant tumor e.g., in mice, and a process for the preparation of the same.

2. Description of the Prior Art

As for the remedies for malignant tumor or cancer (antitumor agents) many drugs have hitherto been known; however, these drugs have a disadvantage that they can not be administered enough to destroy tumor cells, because they have a toxic effect not only upon tumor cells but also upon normal cells to a considerable degree. Several attempts have been made to overcome this disadvantage by combining an antitumor agent or a protein toxin having cytotoxicity with a specific carrier in order to have them selectively absorbed by tumor cells. There exists an antitumor antibody (antitumor immunoglobulin), though very small in amount, in the blood of a cancer patient or on the surface of tumor cells. An antitumor antibody can also be obtained by immunizing an animal with the tumor cells and absorbing the obtained antiserum with the human normal cells. Antitumor antibodies, whether autochthonus, allogeneic, or xenogeneic, are not always capable of displaying a cytotoxic effect against tumor cells; however, they have a common nature of combining with tumor cells with an extremely high selectivity. Antitumor antibodies, therefore, have been used as a carrier to have an antitumor agent or a protein toxin absorbed by tumor cells selectively.

For instance, Japanese Patent Application Laid-open No. 144723/76 discloses, as an antitumor drug, a conjugate of antibody and antitumor drug in which such antitumor drug as daunomycin, etc. is bound covalently with Fab' dimer of antitumor immunoglobulin. This conjugate is superior in that it carries the antitumor drug selectively to the target tumor cells; however, since an antitumor drug itself such as daunomycin, etc. bound with the antibody (Fab' dimer) still exerts cytotoxic effects not only against tumor cells but also against normal cells, it is not satisfactory in view of destroying tumor cells only, and its cytotoxicity itself is not always sufficient either.

Studies have also been made to use diphtheria toxin, which is one of the protein toxins having much stronger toxicity, in the place of an antitumor drug.

For instance, F. L. Moolten et al. report that they prepared a conjugate by conjugating rabbit anti-SV40 antibody to a diphtheria toxin with glutaraldehyde as a coupling agent and were able to protect hamsters challenged with SV40-transformed 3T3 cells from developing tumors by administering the conjugate to hamsters (Journal of the National Cancer Institute, Vol. 55, pp. 473-477, 1975).

P. E. Thorpe et al. report that the conjugate prepared by coupling diphtheria toxin to antilymphocytic antibody by means of chlorambucil greatly reduced the protein synthesis of human lymphoblastoid cells, CLA4. (Nature, vol. 271, pp. 752-754, 1978). The results of these studies show that a conjugate of diphtheria toxin and antibody displays toxicity against the tumor cells selectively. However, these conjugates, when used as an antitumor drug, are believed to have some disadvantages as cited below. First, xenogenic antibody (immunoglobulin) has a strong antigenicity in the human body and induces the formation of anti-xenogeneic immunoglobulic antibody which deactivates the antitumor activity and further causes an anaphylaxis shock. The second of the disadvantages is that the nonspecific toxicity of diphtheria toxin is not nullified. More particularly, the object of these methods is to conjugate diphtheria toxin on the surface of tumor cells by the aid of antitumor antibody; however, since the conjugate contains the whole molecule of diphtheria toxin in its composition, it tends to bind with normal cell surface receptors for diphtheria toxin and display cytotoxicity against the normal cells. Thirdly comes the disadvantage which is found in the method of cross-linking the antibody with the diphtheria toxin. Many of the cross-linking agents such as glutaraldehyde, toluene diisocyanate, diethyl malonimidate, chlorambucil, etc. effect cross-linking not only between the antibody and the toxin but also between antibody and antibody, and toxin and toxin, and moreover, they effect the formation of intramolecule bonds in the antibody and in the toxin molecule, thus causing the formation of undesirable products and decrease or loss of the antitumor activity.

SUMMARY OF THE INVENTION

The present inventors have achieved this invention as a result of their earnest research work to overcome such disadvantages as found with the prior art by developing an antitumor substance which displays strong cytotoxicity against, for example, mice tumor cells selectively.

The present invention relates to an antitumor protein hybrid, composed of a moiety which is substantially the fragment Fab of an antitumor immunoglobulin and a moiety which is the subunit A of ricin, which is expressed by the following formula (I):

$$\text{Fab} \text{-}(S_1 \text{-}(X)_n \text{-} S_2 \text{-} RA)_m \qquad (I)$$

(where Fab indicates a moiety which is substantially the fragment Fab of an antitumor immunoglobulin; RA indicates a moiety which is the subunit A of ricin; X indicates a divalent organic radical; $S_1$ and $S_2$ are both sulfur atoms, $S_1$ indicating a sulfur atom arising from the —S—S— bond in an immunoglobulin and $S_2$ a sulfur atom arising from the —S—S— bond in ricin; n stands for 0 or 1 and m stands for a integer of 1 to 5), and a process for preparing said antitumor protein hybrid, which process comprises binding the sulfur atom in said fragment Fab with the sulfur atom in said subunit A directly or indirectly.

DESCRIPTION OF THE PREFERRED EMBODIMENTS

What is called antitumor immunoglobulin in the present invention is a protein (immunoglobulin) which has an antibody activity prepared from, for instance, the serum of a patient with cancer or serum obtained from such animals as monkeys, horses, cows, goats, sheep, rabbits, etc. which are hyperimmunized with cancer cells or cancer antigen according to a publicly known method such as the Cohn ethanol fractionation method, ammonium sulfate fractionation method, ion-exchange chromatography, etc. Or it is a protein having an antibody activity of high selectively to cancer antigen obtained from a culture fluid of hybridomas or from a serum or ascites of animals inoculated with hybridomas which are prepared by fusing antibody-producing lymphocytes obtained from an animal immunized with cancer cells or cancer antigen to fuse, for instance, with myeloma cells (See, for instance, H. Koprowski, et al., Proc. Natl. Acad. Sci. U.S.A., Vo. 75, No. 7, pp 3405–3409, 1978; Herlyn, et al., ibid., Vol. 76, pp 1438–1442, 1979; M.-Y. Yeh, et al., Proc. Natl. Acad. Sci. U.S.A., Vol. 76, No. 6, pp 2927–2931, 1979; R. H. Kennett, et al., Science, Vol. 203, pp 1120–1121, 1979.) A protein, which has antibody activity, prepared by isolating an antitumor antibody from a tumor tissue with a denaturant such as a surface active agent, etc., followed by the same processing procedure as mentioned above, is also included under the antitumor immunoglobulin according to the present invention.

Figure 1:
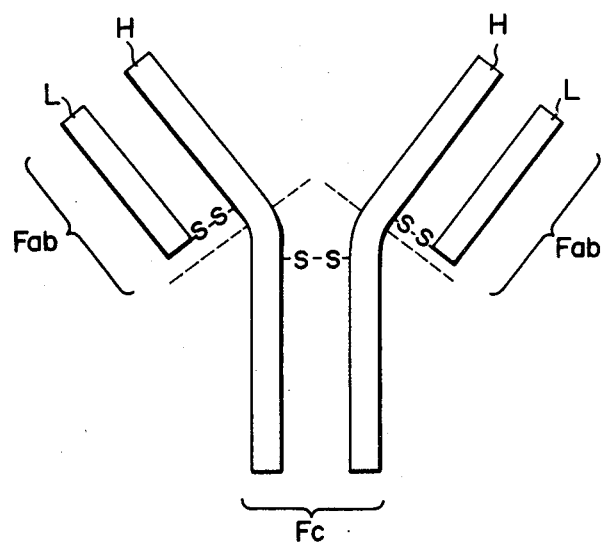
In FIG. 1 is a pictorial drawing of a type specimen to show a basic structure of the immunoglobulin and FIG. 2 is a pictorial drawing of a type specimen to show a structure of human immunoglobulin IgG1.

It is known that there are five major classes of immunoglobulins, IgG, IgA, IgM, IgD and IgE, and that their basic structure comprises, as shown by a pictorial drawing of a type specimen in FIG. 1, two L chains which are indicated by L in the figure and two H chains indicated likewise by H, all chains being bound with at least three disulfide bonds (—S—S— bonds). To explain the basic structure of the immunoglobulin shown in FIG. 1, it consists of Fab parts which are shown by Fab in the figure and an Fc part shown by Fc; Fab parts have an antibody activity (what is called antitumor activity in the present invention), or more particularly an ability to selectively couple to the antigen; Fc part has an ability to couple to complements or Fc receptors on the cell membrane.

Figure 2:
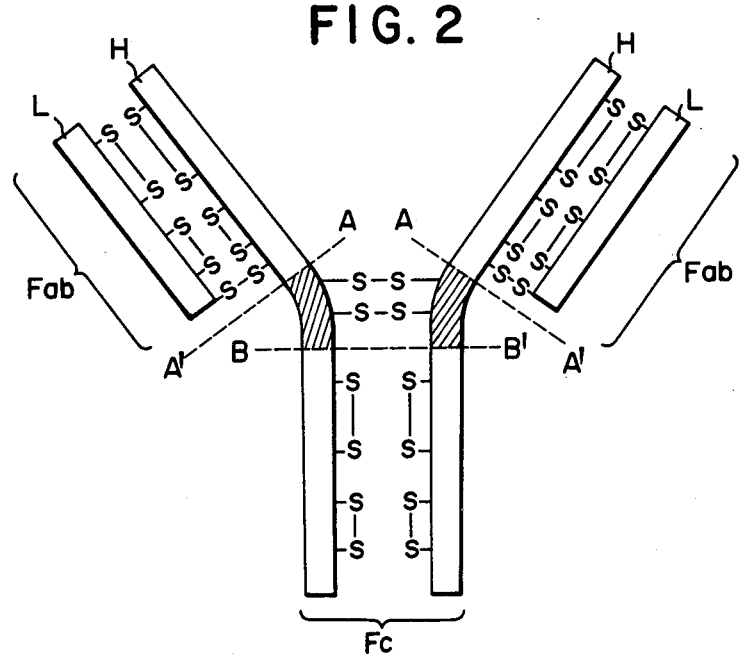

The moiety substantially comprising the fragment Fab which is one moiety of the antitumor protein hybrid of the present invention corresponds to the moiety comprising the fragment having an antibody activity arising from said Fab part of the immunoglobulin. For instance, it is known that IgG1, which is typical of human immunoglobulins, has a structure shown by a pictorial drawing of a type specimen of FIG. 2 and, when subjected to papain digestion in the presence of cystine, this immunoglobulin is cleaved on the broken lines A—A' into two Fab fragments and one Fc fragment as shown in FIG. 2, and the Fab fragments thus obtained can be used as fragment Fab in the present invention. When said IgG1 is treated with pepsin, it is cleaved on the broken line B—B' as shown in FIG. 2, to produce a dimer, (F(ab')₂), of Fab' part consisting of the Fab part and the hinge part which is shaded with oblique lines in the figure. Two Fab' fragments can also be obtained by cleaving the disulfide bond in the hinge part reductively, for instance, with the use of a thiol reagent or by cleaving it by means of sulfonation with sulfite ions. Since this Fab' fragment has an antibody activity like Fab fragment (though it does not have an ability to couple to complements), it can be used as fragment Fab of the present invention. In the present invention, so far as the fragment Fab has an antibody activity, said Fab fragment or Fab' fragment may be the one chemically modified.

Also, substantial fragment Fab having at least one mercapto radical can be converted into a fragment Fab having an active disulfide radical which is expressed by the following formula (V):

$$-S-Z \qquad (V)$$

(where Z indicates

(where Z indicates

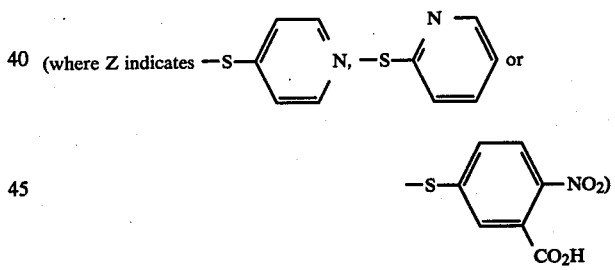

by allowing it to react with 2,2'-dithiopyridine, 4,4'-dithiopyridine, or 5,5'-dithio-bis(2-nitrobenzoic acid) (Ellman's reagent) and the thus converted fragment Fab can be used as the fragment Fab of the present invention.

The thus obtained fragment Fab is used for the preparation of antitumor protein hybrid according to the present invention just as it is so long as it has at least one thiol radical (—SH), S-sulfo radical (—S—SO₃⁻), or active disulfide radical in the fragment but in other cases it is used after it has been changed into a fragment having at least one thiol radical, S-sulfo radical, or active disulfide radical by cleaving at least one of the disulfide bonds in the chains (in the H chains or the L chains) and the disulfide bonds between the chains (between the H chains and the L chains) according to a publicly known method. The number of thiol radicals, S-sulfo radicals, or active disulfide radicals in the fragment Fab should preferably be in the range of 1–5 (corresponding to m=1-5 in the formula (I)) and it is especially preferable to have the number of thiol radicals, S-sulfo radicals, or active disulfide radicals which are formed by cleaving the bonds between the chains within the range of 1-2 (corresponding to m=1-2 in the formula (I)).

Figure 3:
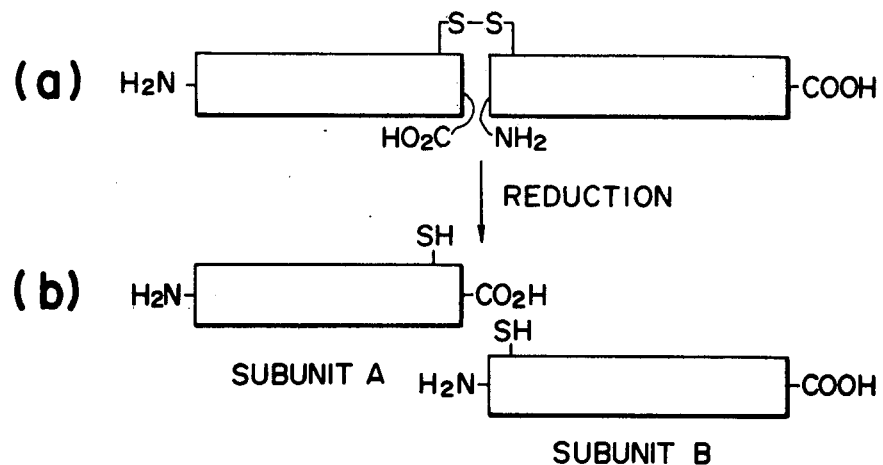
In FIG. 3, (a) is a pictorial drawing of a type specimen to show a structure of ricin and (b) is those of subunits A and B.

What is called ricin in the present invention is a protein toxin which can be extracted and purified from the seeds of Ricinus Communis according to a publicly known method, for instance, a method proposed by S. Alsnes and A. Pihl in Biochemistry, vol. 12, pp. 3121-3126, 1973. Ricin consists of subunit A having a molecular weight of 32,000 and subunit B having a molecular weight of 34,000, both of which are connected to each other by a disulfide bond (FIG. 3, (a)). When ricin is treated with a reductant, it is divided into subunit A and subunit B, each having at least one mercapto radical (—SH) as shown in FIG. 3, (b). Before ricin is divided apart, it has a very strong toxicity against animals; however, subunit B alone has only a weak toxicity and subunit A has a weaker toxicity. It is assumed that ricin displays its cytotoxicity inhibiting the biosynthesis of protein by deactivating a component which is indispensable for lengthening the peptide chains. Subunit A has an activity to inhibit the biosynthesis of protein in the cell-free system, while subunit B does not have such activity but an ability to couple to the receptor of a cell which is not seen with subunit A. In the present invention, subunit A is used.

In the present invention, when fragment Fab of antitumor immunoglobulin having at least one thiol radical, S-sulfo radical, or active disulfide radical in the fragment is made to react directly with subunit A of ricin having at least one thiol radical in the fragment under the reaction conditions mentioned later, antitumor protein hybrids expressed by the undermentioned formula (II′) which corresponds to the aforementioned formula (I) wherein n=0 are obtained.

(where the definitions of Fab, RA, m, $S_1$ and $S_2$ are the same as those given in case of formula (I)). Of these, the one which has a structure expressed by the following formula (II) is especially preferable from the viewpoint of ease of preparation, separation and purification:

(where the definitions of Fab, RA, $S_1$ and $S_2$ are same as those given in case of formula (I): p indicates 1 or 2).

In the present invention, the divalent organic radical, which is expressed by X where n=1 in the aforementioned formula (I), means an organic radical arising from a cross-linking agent having in the molecule at least two functional groups capable of forming a sulfide bond (—S— bond) by reacting with a thiol radical (—SH). Such cross-linking agents include, for instance, a dimaleimide compound which is expressed by the undermentioned formula (III) and a bishalocarbonyl compound which is expressed by the formula (IV) as the most preferable ones.

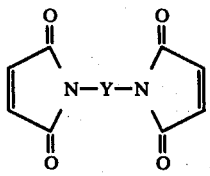

(where Y indicates a divalent organic radical).

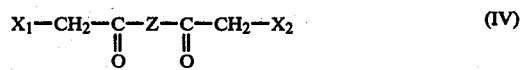

(where Z indicates a divalent organic radical, $X_1$ and $X_2$ are the same or differ from each other indicating bromine or iodine).

Specific examples of dimaleimide compound expressed by the abovementioned formula (III) are, for instance, N,N′-(1,2-phenylene)dimaleimide, N,N′-(1,4-phenylene)dimaleimide, 4,4′-bis(maleoylamino) azolenzene, and bis(N-maleimidomethyl)ether. Specific examples of bishalocarbonyl compound expressed by the formula (IV) are N,N′=alkylenebis(bromoacetamide) and N,N′-alkylenebis(iodoacetamide) (wherein the alkylene radical has 2-15 carbon atoms).

The antitumor protein hybrid of the present invention can be prepared according to the methods given in the following.

(1) A method to make a substantial fragment Fab which has at least one S-sulfo radical or active disulfide radical expressed by the aforementioned formula (V) in the fragment react with a subunit A which has at least one thiol radical in the fragment.

In this method, it is preferable to use a ratio of 0.3 to 3 moles of subunit A to 1 mole of fragment Fab. The reaction can be conducted by mixing fragment Fab and subunit A in a buffer whose pH is in the range of 5-10 to make a total protein concentration of 0.5 to 100 mg/ml (more preferably 1 to 20 mg/ml) and leaving the mixture standing at 0° to 60° C. or dialyzing the reaction mixture against the buffer having the same pH value as the reaction mixture. The reaction time generally extends over a period of 30 minutes to 3 days, depending upon the scale and conditions of the reaction. The separation of the hybrid thus composed of fragment Fab and subunit A from the reaction mixture and the purification can be carried out according to a usual procedure, for instance, dialysis or column chromatography of a molecular sieve effect.

The method mentioned above allows the reaction to proceed smoothly under very moderate conditions to produce a highly purified hybrid. The method also has the advantage of permitting the selective formation of hybrid composed of fragment Fab and subunit A (as compared to the formation of hybrid between fragments Fab themselves or between subunits A themselves coupled by the disulfide bond).

(2) A method for binding a substantial fragment Fab which has at least one thiol radical in the fragment and a substantial subunit A which has at least one thiol radical in the fragment with the use of either of the aforementioned cross-linking agents expressed by the formulae (III) and (IV).

In the above method, the reaction can be conducted by bringing fragment Fab, cross-linking agent and subunit A into contact with each other simultaneously, however, it is preferable to carry out the preparation of the hybrid by making subunit A react with the reaction product obtained by first allowing fragment Fab to react with the cross-linking agent or by making fragment Fab react with the reaction product obtained by first allowing subunit A to react with the cross-linking agent. In the former case, it is preferable to use 0.8 to 6 moles of the cross-linking agent and subunit A respectively to 1 mole of fragment Fab. In the latter case, it is preferable to use 0.8 to 3 moles of the cross-linking agent and 0.2 to 3 moles of fragment Fab to 1 mole of subunit A. The reaction is started at 0° to 60° C. with stirring with the addition of the cross-linking agent dissolved in a small amount of solvent such as N,N-dimethylformamide, dimethyl sulfoxide, 1,2-dimethoxyethane, methanol, ethanol, acetone, etc. to a solution of fragment Fab or subunit A buffered at a pH of 6 to 10 (the protein concentration being preferably controlled to 0.5 to 100 mg/ml, or more preferably to 1 to 20 mg/ml). After the removal of the cross-linking agent left unreacted by means of dialysis or column chromatography of a molecular sieve effect, another component (subunit A or fragment Fab) solution buffered at a pH of 6 to 10 (the preferable ranges of protein concentration being the same as mentioned above) is added to carry out the reaction at 0° to 60° C. The separation, and purification as well, of the thus obtained hybrid of fragment Fab and subunit A from the reaction mixture can be effected according to a usually adopted method such as column chromatography of a molecular sieve effect.

Figure 4:
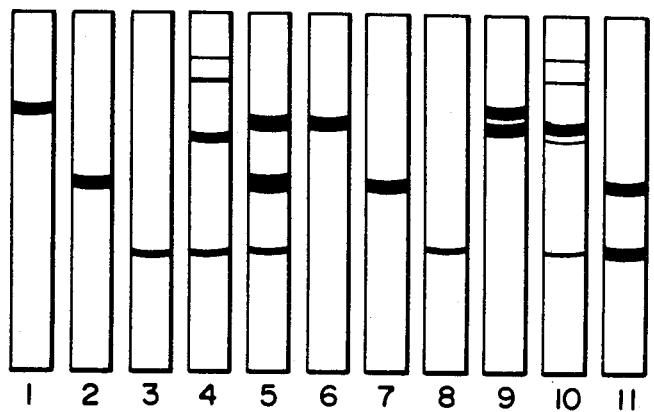
FIG. 4 shows patterns of electrophoresis conducted with sodium dodecyl sulfate-polyacrylamide gel. Disc 1 shows F(ab')₂, disc 2 Fab', disc 3 subunit A, disc 4 a polymer of subunit A, and disc 5 a reaction mixture solution of Fab' and subunit A (Example 1) respectively. Also, disc 6 shows peak I of FIG. 4, disc 7 peak II of FIG. 5, disc 8 peak III of FIG. 5, disc 9 a mixture of F(ab')₂ and peak I, disc 10 a mixture of a polymer of subunit A and peak I, and disc 11 a product obtained by moderately reducing the protein of peak I with 2-mercaptoethanol respectively.

(3) A method in which fragment Fab of the antitumor immunoglobulin which has at least one thiol radical in the fragment and subunit A of ricin which has at least one thiol radical in the subunit are subjected to the oxidative reaction in the presence of each other to have them both bound by the disulfide bond. As for the oxidative reaction, any of the air oxidation method, method of oxidation with the use of o-iodobenzoic acid and method in which oxidation is effected with o-phnanthroline and cupric sulfate may be adopted.

In the present invention, (1) and (2) of the abovementioned methods are especially preferable.

The antitumor protein hybrid of the present invention consists of a moiety comprising subunit A which demonstrates toxicity against tumor cells and a moiety substantially comprising fragment Fab which selectively recognizes a tumor cell and works as a carrier to guide said subunit A to the tumor cell and take subunit A into the cell as well and this hybrid has excellent characteristics mentioned below.

(1) Since the hybrid of the present invention does not contain the Fc part of the immunoglobulin, nonspecific binding to Fc receptors on the cell membrane with the Fc part is avoided and this fact allows the antibody activity or performance of the fragment Fab to selectively couple to the antibody to be demonstrated predominantly.

(2) It is known that, when a xenogeneic immunoglobulin is used, it is the Fc part that has the strongest antigenicity. In case of the hybrid according to the present invention, since it does not contain the Fc part of the immunoglobulin, the antigenecity of the xenogeneic immunoglobulin is reduced remarkably.

(3) It is known that, in case of the ricin molecule, it is the subunit B that has the ability to couple to the receptor of cells (normal cells and tumor cells) and that the subunit A can be taken into the cell by means of the coupling of the subunit B to the cell membrane to demonstrate the cytotoxicity. However, since the hybrid of the present invention does not contain the subunit B, the hybrid of the present invention scarcely demonstrates cytotoxicity to normal cells. Furthermore, since it does not contain the subunit B, the antigenecity of ricin is also reduced.

(4) The hybrid of the present invention has a moiety substantially comprising the fragment Fab obtained from the antitumor immunoglobulin and this moiety specifically recognizes a tumor cell and cause the tumor cell to take in specifically the moiety comprising the subunit A of ricin. The subunit A thus taken in demonstrates a remarkable cytotoxicity to the tumor cell.

The present invention is described in detail by the following examples.

Example 1

(a) Preparation of fragment Fab' of antitumor immunoglobulin

Mouse leukemia L 1210 cells transplanted successively on DBA/2 Cr mice were taken out of the ascites of a DBA/2 Cr mouse. An emulsion prepared from about $10^6$ of those cells and Freund's complete adjuvant (immuno adjuvant) was intravenously injected into a rabbit. After that $10^6$ L 1210 cells, together with the adjuvant, were subcutaneously injected three times at one-week intervals, and the rabbits were bled seven days and ten days after the day of final injection. The blood thus obtained was mixed and serum was separated from the mixed blood and was inactivated at 56° C. for 30 minutes. 200 ml of saturated aqueous ammonium sulfate solution was added to 200 ml of thus obtained anti-L 1210 antiserum at 4° C. and the precipitate (anti-L 1210 immunoglobulin) was separated by means of centrifugation. The precipitate thus obtained was dissolved in 50 ml of 0.01 M phosphate buffer (pH 7.6) and was sufficiently purified by dialysis against the same buffer to obtain a solution of anti-L 1210 immunoglobulin. The solution was subjected to DEAE cellulose column chromatography (column size 3 cm×94 cm) equilibrated with the same phosphate buffer to obtain a solution containing IgG as an unadsorbed fraction. A solution of this anti-L 1210 IgG (1.2 g) in 40 ml of 0.1 M acetate buffer (pH 4.5) was prepared, and to the solution 24 mg of pepsin was added to effect pepsin digestion at 37° C. for about 18 hours. The digestion product was subjected to Sephadex G200 column chromatography (column size 3.5 cm×140 cm) over silane to take out protein eluted at molecular weight of about 100,000. It was confirmed that this was a pure fragment $F(ab')_2$ by means of electrophoresis with sodium dodecyl sulfate-polyacrylamide gel (hereinafter referred to as SDS.PAGE) (See FIG. 4, disc 1). SDS.PAGE was carried out according to a method proposed by K. Weber and Mr. Osborn in the Journal of Biological Chemistry, vol. 244, pp. 4406–4412, 1969. However, the present electrophoresis was conducted with 6 M urea contained in the solution togethe with 0.1% sodium dodecyl sulfate with the gel concentration kept at 6%. 0.02 ml of 150 m M 2-mercaptoethanol was added to 2.0 ml of 0.01 M tris.HCl-0.14 M sodium chloride-2 M ethylenediaminetetraacetic acid (pH 8.3) containing 18.4 g of thus obtained fragment $F(ab')_2$ to effect reduction at 37° C. for one hour. The reduction product was subjected to Sephadex G25 column chromatography (1.0 cm×20 cm) equilibrated with 5 m M acetate buffer- 0.14 M sodium chloride-1 m M ethylenediaminetetraacetic acid (pH 5.5) to remove 2-mercaptoethanol to give fragment Fab' having one thiol radical (See FIG. 4, disc 2).

(b) Preparation of fragment Fab' having a 3-carboxy-4-nitrophenylthio radical

After F(ab')$_2$ was reduced exactly according to the method mentioned above, 0.2 ml of an ethanol solution containing 50 m M 5,5'-dithiobis(2-nitrobenzoic acid) was added to 2.0 ml of thus obtained protein solution to conduct the reaction at room temperature for 50 minutes. This reaction mixture was subjected to Sephadex column chromatography referred to in the preceeding (a) for the purpose of removing substances of low molecular weight to obtain Fab' which has a 3-carboxy-4-nitrophenylthio radical.

(c) Preparation of ricin subunit A

Extraction and purification of ricin from the seeds of Ricinus Communis and separation of subunit A from ricin were effected according to the method of S. Olsnes and A. Pihl (Biochemistry, vol. 12, pp. 3121–3126, 1973). Since the obtained subunit A solution contained 2-mercaptoethanol, the solution was, immediately before its use, subjected to Sephadex G25 column chromatography described in the foregoing (a) to remove 2-mercaptoethanol. Neither subunit B nor intact ricin was detected in this subunit A solution on its SDS.PAGE (See FIG. 4, disc 3).

Figure 5:
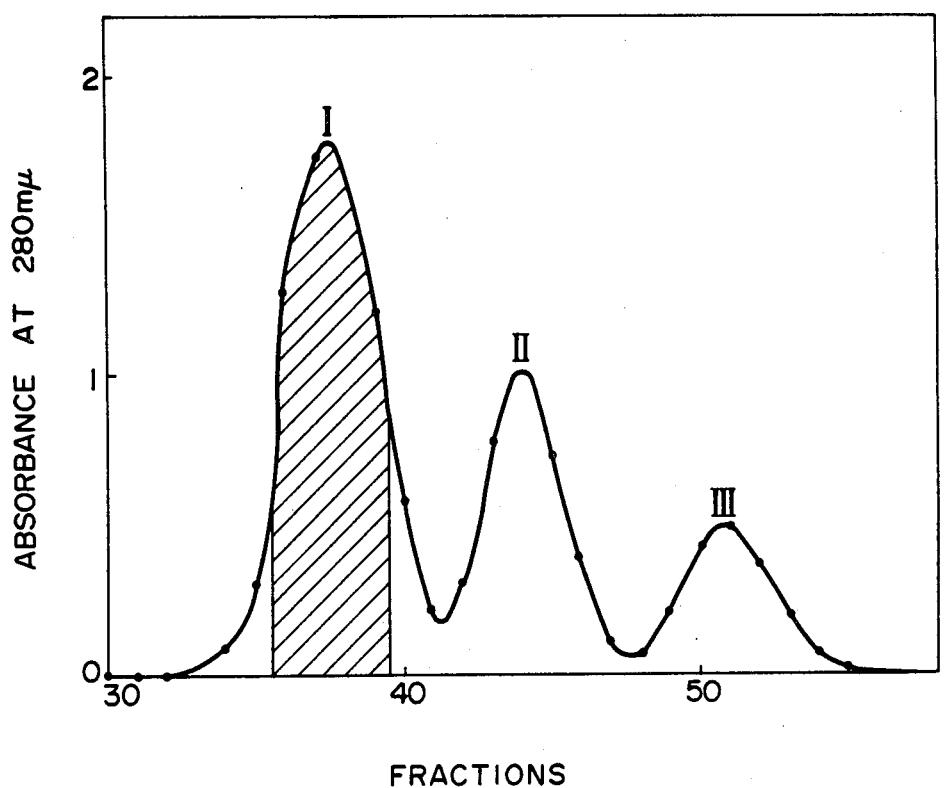
FIG. 5 shows the elution pattern obtained by Sephadex G150 column chromatography conducted for the reaction mixture of fragment Fab' of anti-L1210 immunoglobulin and subunit A of ricin, and the protein hybrid of the present invention is included in the shaded part.

(d) Preparation of antitumor protein hybrid 1.8 ml of 5 m M acetate buffer-0.14 M sodium chloride-1 m M ethylene diaminetetraacetic acid (pH 5.5) containing 13.3 mg of Fab' having an active disulfide radical obtained in the preceding (b), 1.8 ml of 5 m M acetate buffer-0.14 M sodium chloride-1 m M ethylenediaminetetraacetic acid (pH 5.5) containing 6.5 mg of subunit A obtained in the preceding (b), and 0.3 ml of 0.4 M phosphate buffer-0.01 M ethylenediaminetetraacetic acid (pH 7.23) were mixed together and allowed to stand at room temperature for 4.5 hours. After the addition of 5 mg of iodoacetamide, the mixture was left standing at room temperature for 15 minutes and then subjected to sephadex G150 (superfine) column chromatography (1.4 cm×90 cm) equilibrated with saline. 2.1-ml fractions were collected and the absorbances at 280 mμ of the respective fractions were measured, the results of which measurements are shown in FIG. 5. There are three peaks in the figure and they are named peaks I, II, and III from the left, whose protein identification was made by means of SDS-PAGE. Peak II is fragment Fab' as per disc 7 and peak III is subunit A as per disc 8. Peak I shows one band as in disc 6 at a position near to that of F(ab')$_2$ or dimer of subunit A. However, when either peak I and F(ab')$_2$ or peak I and dimer of subunit A are mixed and subjected to electrophoresis, the three kinds of proteins show themselves clearly differing from each other as per discs 9 and 10. Furthermore, when peak I is reduced moderately with 2-mercaptoethanol, it divides into Fab' and subunit A as per disc 11. From the above, it has been confirmed that peak I is a hybrid comprising Fab' and subunit A coupled together by a disulfide bond at the ratio of 1:1.

(e) Cytotoxicity of antitumor protein hybrid

Fractions falling under the shaded part of FIG. 5 were collected to obtain saline containing the protein hybrid (1.1 mg/ml) of the present invention. This aqueous solution was used for measuring cytotoxicity of the protein hybrid of the present invention against mouse lukemia L 1210 cells.

In the culture wells having a bottom area of 2.0 cm$^2$, 1.4 ml of the medium RPMI 1640 (containing 10% fetal calf serum and 20 μM 2-mercaptoethanol), 0.1 ml of L 1210 cell suspension (5×10$^5$ cells/ml), and 0.1 ml of the test sample (ricin or protein hybrid of the present invention) were mixed, and furthermore, as occasion may require, anti-rabbit Fab' antibody (130 μg/ml) (which antibody is obtained by immunizing a goat with rabbit Fab') or 0.1 mol (final concentration) of α-lactose may be added as a toxicity inhibitor. The culture was carried out a 37° C. in an atmosphere of 5% CO$_2$ for 42 hours. Thereafter, the cytotoxicity was observed under a phase-contrast microscope. When all of the globular cells were found damaged, the result is indicated by +++; when 90–50% were found damaged, the result is indicated by ++; when 50–10% were found damaged, the result is indicated by +; and when the result was the same as that of the control, it is indicated by —, The results are shown in Table 1.

TABLE 1

Cytotoxicity of antitumor protein hybrid against L 1210 cells

| Inhibitor | (Ricin (ng/ml)) | | | Protein hybrid of the present invention (ng/ml) | | |
|---|---|---|---|---|---|---|
| | 70 | 7 | 0.7 | 7000 | 700 | 70 |
| None | +++ | ++ | + | ++ | + | — |
| Anti-rabbit Fab' antibody | +++ | ++ | + | — | — | — |
| α-lactose | ++ | — | — | ++ | + | — |
| Anti-rabbit Fab' antibody + α-lactose | ++ | — | — | — | — | — |

As Table 1 shows clearly, ricin itself has nonselective strong toxicity and this toxicity is not influenced by anti-rabbit Fab' antibody but reduced by α-lactose which is a substance to inhibit the binding of ricin and cells.

On the other hand, though the protein hybrid of the present invention has a toxicity weaker than ricin, it still has enough cytotoxicity. And from the fact that this toxicity can be completely suppressed by the anti-rabbit Fab' antibody, it is known that the moiety comprising fragment Fab' of the protein hybrid plays an important role in this cytotoxicity. It is also made known that, since this toxicity, different from ricin, is quite free from the influence of α-lactose, the toxicity does not arise from any contamination with ricin and that the toxicity is displayed by a mechanism different from that of ricin. From these facts, the protein hybrid of the present invention is expected to display specific toxicity against tumor cells which the fragment Fab' can recognize.

Example 2

(a) Preparation of fragment Fab' having 4-pyridylthio radical 0.2 ml of an ethanol solution containing 50 m M 4,4'-dipyridyldisulfide was added to 2.0 ml of the protein solution after the reduction of F(ab')$_2$ conducted according to Example 1, (a), and the mixture was allowed to react at a room temperature for 30 minutes. This reaction solution was subjected to Sephadex G25 column chromatography to remove substances of low molecular weight, thus obtaining Fab' having a 4-pyridylthio radical.

(b) Preparation of antitumor protein hybrid 12.5 mg of fragment Fab' having an active disulfide radical obtained in the preceding (a) and 6.1 mg of subunit A of ricin obtained in Example 1, (c), were mixed in 1.57 ml of 0.1 M phosphate buffer-2 m M ethylenediaminetetraacetic acid (pH 6.6) to carry out the coupling reaction at room temperature for 3 hours. After that, the same procedures as taken in Example 1 were followed to obtain the protein hybrid, the object of the present invention, comprising fragment Fab' and subunit A linked by a disulfide bond.

Example 3

13.1 mg of fragment Fab' having a thiol radical obtained in Example 1, (a), and 5.8 mg of subunit A of ricin obtained in Example 1, (c), were mixed in 3.6 ml of 0.1 M glycine buffer-2 m M ethylenediaminetetraacetic acid (pH 9.15) to carry out the coupling reaction at room temperature for 8 hours. Thereafter, the same procedures as taken in Example 1 were followed to obtain the protein hybrid, the object of the present invention, comprising fragment Fab' and subunit A linked by a disulfide bond.

Example 4

(a) Preparation of fragment Fab' having an S-sulfo radical 1.7 mg of sodium sulfite and 0.7 mg of sodium tetrathionate were added to 2.0 ml of 0.1 M Tris.HCl-2 m M ethylenediaminetetraacetic acid (pH 7.8) containing 18.3 mg of fragment F(ab')$_2$ obtained in Example 1, (a), to carry out the sulfonation reaction at 37° C. for one hour. The sulfonated solution was subjected to Sephadex G25 column chromatography according to Example 1, (a), to obtain fragment Fab' having an S-sulfo radical.

(b) Preparation of antitumor protein hybrid 130 mg of fragment Fab' having an S-sulfo radical obtained in the abovementioned (a) and 5.6 mg of subunit A of ricin obtained in Example 1, (c), were mixed in 1.82 ml of 5 m M acetate buffer-0.14 M sodium chloride-1 m M ethylenediaminetetraacetic acid (pH 5.5). The admixture was dialyzed at 4° C. for three days against 1 l of 0.1 M glycine buffer-2 m M ethylenediamine tetraacetic acid (pH 9.15) to effect the reaction. Thereafter, the same procedures as taken in Example 1 were followed to obtain the protein hybrid, the object of the present invention, comprising fragment Fab' and subunit A linked each other by a disulfide bond.

Example 5

A fragment Fab' solution (7 mg/ml) was prepared by dissolving fragment Fab' of anti-L 1210 immunoglobulin IgG having one thiol radical obtained in Example 1, (a), in a mixed solution consisting of 2 parts by volume of 0.1 M sodium phosphate buffer (pH 6.0) and 1 part by volume of acetone. A suspension of a cross-linking agent, N,N'-(1,4-phenylene)dimaleimide (PDM) in acetone (5 mg/ml) was separately prepared.

0.1 ml of the PDM solution was added dropwise to 1.0 ml of the fragment Fab' solution and the reaction was allowed to proceed at room temperature for 30 minutes. Acetone was removed from the obtained reaction mixture with the use of an evaporator and further insoluble substances were removed by means of centrifugation conducted at 10,000 rpm for 30 minutes. The solution thus obtained was subjected to Sephadex G25 column chromatography equilibrated with 0.1 M sodium phosphate buffer (pH 7.0) to give a solution of fragment Fab' having a PDM residue.

The thus obtained solution of fragment Fab' having a PDM residue was admixed with subunit A of ricin having one thiol radical prepared according to Example 1, (c), in such a way as to have the fragment Fab'-subunit A molar ratio of 1:0.7 and the coupling reaction was allowed to proceed at 4° C. for 24 hours and further at 37° C. for one hour. The obtained reaction solution was subjected to Sephadex G150 column chromatography under the same conditions as Example 1. As a result of measurement of the absorbance at 280 m$\mu$ of the fractions, three peaks were observed as in the case of Example 1. The 37th and 38th fractions which came under peak I showed the precipitation reaction with goat anti-rabbit IgG anti-serum and also with guinea pig anti-ricin A antiserum. It was confirmed that their molecular weight was 76,000 on electrophoresis conducted with sodium dodecyl sulfate and also that they could not be divided into fragment Fab' and subunit A when treated with 2-mercaptoethanol. From these facts it was confirmed that the 37th and 38th fractions contained the protein hybrid aimed at for the object of the present invention, or more particularly, that these fractions contained the protein hybrid in which fragment Fab' and subunit A were linked together by PDM, a cross-linking agent, via the respective sulfur atoms. It was also found that this protein hybrid had cytotoxicity against L 1210 almost equal to potency to the one obtained in Example 1.

Example 6

According to Example 5, antitumor protein hybrid was obtained, in which fragment Fab' and subunit A were linked to each other by a cross-linking agent of N,N'-(1,2-phenylene)dimaleimide via the respective sulfur atoms, wherein N,N'-(1,3-phenylene)dimaleimide was used in the place of PDM which was used in Example 5.

Example 7

According to Example 5, antitumor protein hybrid was obtained, in which fragment Fab' and subunit A were linked to each other by a cross-linking agent of 4,4'-bis(maleoylamine)azobenzene via the respective sulfur atoms, wherein 4,4'-bis(maleoylamino)azobenzene was used in the place of PDM which was used in Example 5.

Example 8

Fragment Fab' of anti-L 1210 immunoglobulin IgG having one thiol radical obtained according to Example 1, (a), was dissolved in a mixed solution consisting of 3 parts by volume of 0.1 M sodium phosphate buffer (pH 7.5) and 1 part by volume of N,N-dimethylformamide at the concentration of 7 mg/ml to prepare a solution of fragment Fab'. Besides this solution, a solution was prepared by dissolving a cross-linking agent of N,N'-ethylenebis(iodoacetamide) in N,N-dimethylformamide at a concentration of 6 mg/ml.

0.1 ml of the N,N'-ethylenebis(iodoacetamide) solution was added dropwise to 1.0 ml of the fragment Fab' solution, and the reaction was allowed to proceed at room temperature for one hour. The obtained reaction mixture was purified by column chromatography on Sephadex G25 equilibrated with 0.1 M sodium phosphate buffer (pH 7.5) to give a solution of fragment Fab' having N,N'-ethylenebis(iodoacetamide) residue.

The subunit A of ricin having one thiol radical prepared according to Example 1, (c), was added to the solution of fragment Fab' having N,N'-ethylenebis(iodoacetamide) residue obtained as mentioned above to make the molar ratio of fragment Fab' having N,N'-ethylenebis(iodoacetamide) residue to subunit A 1:0.5 and mixed. After that, the procedures were followed as in the case of Example 5 to give the protein hybrid of the present invention in which fragment Fab' and subunit A were linked to each other by a cross-linking agent of N,N'-ethylenebis(iodoacetamide) via the respective sulfur atoms. This protein hybrid had a remarkable cytotoxicity against L 1210 cells almost equal in potency to the one obtained according to Example 1.

Example 9

According to Example 8, antitumor protein hybrid was obtained, in which fragment Fab' and subunit A were linked to each other by a cross-linking agent of N,N'-hexamethylenebis(iodoacetamide) through the medium of the respective sulfur atoms, wherein N,N'-hexamethylenebis(iodoacetamide) was used in the place of N,N'-ethylenebis(iodoacetamide) which was used in Example 8.

Example 10

According to Example 8, antitumor protein hybrid was obtained, in which fragment Fab' and subunit A were linked to each other by a cross-linking agent of N,N'-undecamethylenebis(iodoacetamide) through the medium of the respective sulfur atoms, wherein N,N'-undecamethylenebis(iodoacetamide) was used in the place of N,N'-ethylenebis(iodoacetamide) which was used in Example 8.

Example 11

According to Example 5, antitumor protein hybrid was obtained, in which fragment Fab' and subunit A were linked to each other by a cross-linking agent of bis(N-maleimidemethyl)ether through the medium of the respective sulfur atoms, wherein bis(N-maleimidemethyl)ether was used in the place of PDM which was used in Example 5.

What is claimed is:

1. A process for preparing an antitumor protein hybrid which is expressed by the following formula (II'), which process comprises reacting the substantial fragment Fab of an antitumor immunogloblin which has at least one S-sulfo radical or an active disulfide radical expressed by the following formula (V) with the subunit A of ricin which has at least one thiol radical in the fragment:

$$-S-Z \quad (V)$$

where Z indicates

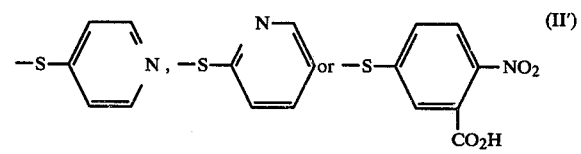

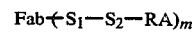

wherein Fab indicates a moiety which is substantially the fragment Fab of an antitumor immunoglobulin; RA indicates a moiety which is the subunit A of ricin; $S_1$ and $S_2$ are both sulfur atoms, $S_1$ indicating a sulfur atom arising from the disulfide bond in the immunoglobulin and $S_2$ a sulfur atom arising from the disulfide bond in ricin; and m represents an integer of 1 to 5.

2. A process for preparing an antitumor protein hybrid which is expressed by the following formula (I'), which process comprises binding the substantial fragment Fab of an antitumor immunoglobulin which has at least one thiol radical in the fragment with the subunit A of ricin which has at least one thiol radical in the fragment with the use of a compound which has at least two functional groups capable of reacting with a thiol radical $$\text{Fab}-(S_1-X-S_2-RA)_m \quad (I')$$

wherein Fab indicates a moiety which is substantially the fragment Fab of an antitumor immunoglobulin; RA indicates a moiety which is the subunit A of ricin; X indicates a divalent organic radical; $S_1$ and $S_2$ are both sulfur atoms, $S_1$ indicating a sulfur atom arising from the disulfide bond in the immunoglobulin and $S_2$ a sulfur atom arising from the sulfide bond in ricin; and m represents a integer of 1 to 5.

3. The process of claim 1, wherein said substantial fragment Fab of an antitumor immunoglobin is the substantial fragment Fab of an antitumor immunoglobin having at least one S-sulfo radical.

* * * * *

UNITED STATES PATENT AND TRADEMARK OFFICE
CERTIFICATE OF CORRECTION

PATENT NO. : 4,450,154
DATED : May 22, 1984
INVENTOR(S) : Yasuhiko Masuho et al

It is certified that error appears in the above-identified patent and that said Letters Patent is hereby corrected as shown below:

On the cover page under "References Cited" "U.S. PATENT DOCUMENTS"

please insert --4,340,535 7/1982 Voisin et al. ......260/112B--.

Signed and Sealed this

Thirteenth Day of November 1984

[SEAL]

Attest:

GERALD J. MOSSINGHOFF

Attesting Officer      Commissioner of Patents and Trademarks